United States Patent [19]

Baerts

[11] Patent Number: 5,515,739

[45] Date of Patent: May 14, 1996

[54] MOLTEN METAL SAMPLER

[75] Inventor: Christiaan Baerts, Beringen-Paal, Belgium

[73] Assignee: Heraeus Electro-Nite International N.V, Houthalen, Belgium

[21] Appl. No.: 192,483

[22] Filed: Feb. 7, 1994

[30] Foreign Application Priority Data

Feb. 9, 1993 [DE] Germany .................. 43 03 688.0

[51] Int. Cl.$^6$ .................................................. G01N 1/12
[52] U.S. Cl. ........................................................ 73/864.55
[58] Field of Search .......................... 73/864.56, 864.53, 73/864.55, 864.57, 864.58, 864.54

[56] References Cited

U.S. PATENT DOCUMENTS

| | | | |
|---|---|---|---|
| 3,994,172 | 11/1976 | Kelsey | 73/864.55 |
| 4,002,069 | 1/1977 | Takemura et al. | 73/DIG. 9 X |
| 4,116,070 | 9/1978 | Falk . | |
| 4,565,101 | 1/1986 | Boron | 73/864.57 |
| 4,699,014 | 10/1987 | Boron | 73/864.55 X |

FOREIGN PATENT DOCUMENTS

| | | |
|---|---|---|
| 0402638 | 12/1990 | European Pat. Off. . |
| 0404291 | 12/1990 | European Pat. Off. . |
| 2254488 | 5/1973 | Germany ............... 73/864.55 |
| 285190 | 12/1990 | Germany . |
| 57-197467 | 12/1982 | Japan . |
| 1-032166 | 2/1989 | Japan . |
| 1150149 | 4/1969 | United Kingdom . |

*Primary Examiner*—Thomas P. Noland
*Attorney, Agent, or Firm*—Panitch Schwarze Jacobs & Nadel

[57] ABSTRACT

A sampler for molten metal has a flat sample chamber arranged in a carrier tube, an inlet duct with an inflow opening arranged on the side of the flat sample chamber facing away from the immersion end of the carrier tube, and a wall surface which forms a sample analysis surface running parallel to the axis of the carrier tube. In order to create a sampler with which high-quality flat samples can be obtained and which can be easily removed from the sampler, a prechamber is arranged inside the carrier tube, at the end of the inlet duct facing away from the immersion end of the carrier tube, above the flat sample chamber and between the inlet duct and the inflow opening. The prechamber has a cross-sectional area transverse to the inflow direction through the inflow opening which is greater than the cross-sectional area of the inflow opening, and a cross-sectional area transverse to the axis of the inlet duct in the vicinity of its inlet which is greater than the cross-sectional area of the inlet of the inlet duct.

14 Claims, 3 Drawing Sheets

MOLTEN METAL SAMPLER

FIELD OF THE INVENTION

The invention concerns a sampler for molten metal with a flat sample chamber, arranged in a carrier tube, which has an inlet duct with an inflow opening arranged on the side of the flat sample chamber facing away from the immersion end of the carrier tube, and which has a sort of wall surface, which forms a sample analysis surface, which runs parallel to the axis of the carrier tube.

BACKGROUND OF THE INVENTION

A sampler of this kind is known from DD 285190, which describes a flat sample chamber, arranged in a carrier tube, whose wall surfaces (which form the analysis surfaces) run parallel to the axis of the carrier tube. The inlet opening into the sample chamber is arranged on the side of the sample chamber facing away from the immersion end. The inlet opening extends inside an inlet duct that runs coaxially with the axis of the carrier tube and is bent over at its upper end, facing away from the immersion end, and passes through the wall of the carrier tube. Through this bent piece, the melt penetrates into the coaxial inlet duct and from there into the sample chamber. After solidification the coaxial inlet duct simultaneously constitutes a pin sample.

Since the sample chamber is formed of two halves, the gases present in the sample chamber before immersion in the melt can escape from the sample chamber through the parting lines between the two chamber halves, but the gases and other contaminants penetrating along with the melt into the sample chamber are also brought into the sample chamber and remain there as inclusions in the sample. These inclusions detract from the quality of the sample and thus the reliability of the sample analysis. The contaminants present in the sample are found not only in the interior of the sample, but also detract from the quality of the sample analysis surfaces since they arise directly in the vicinity of those surfaces. This, however, calls into question an essential advantage of flat sample chambers as compared to compact sample chambers, namely the fact that the sample analysis surface formed by the chamber wall is available for analysis almost without further processing.

A further sampler is known from GB 1,150,149 which describes, in connection with FIG. 6, a flat sample whose analysis surfaces are arranged transversely to the axis of the carrier tube. Since cooling of the sample always proceeds from the outside in (radially to the carrier tube axis), the sample analysis surfaces have different compositions in accordance with the cooling process, depending on the distance of the measurement point from the edge of the surface. With the apparatus described, it is additionally disadvantageous in terms of sampling that the sample chamber acts as a heat sink and causes rapid solidification of the sample and of the molten metal above it. This rapid solidification of the melt present in the sample chamber immobilizes in the sample the contaminants that enter the sample chamber along with the melt, and again negatively affects the analytical result. This rapid solidification process is promoted by the arrangement of the mixing chamber and sample chamber in a shared housing. The shared housing also makes it difficult to remove the sample from the sampler.

The underlying object of the present invention is to provide a sampler for molten metal which allows high-quality flat samples to be obtained and to be easily removed from the sampler.

SUMMARY OF THE INVENTION

According to the invention, the above object is achieved, by arranging inside the carrier tube, at the end of the inlet duct facing away from the immersion end of the carrier tube, above the flat sample chamber and between the inlet duct and the inflow opening, a prechamber whose cross-sectional area transverse to the inflow direction through the inflow opening is greater than the cross-sectional area of the inflow opening, and whose cross-sectional area transverse to the axis of the inlet duct in the vicinity of its inlet is greater than the cross-sectional area of the inlet of the inlet duct. The sampler is suitable, for example, for taking samples of molten metals in a converter. A sample obtained with this type of sampler not only has a highly uniform sample quality, including in particular its surface region, but is also very easy to remove from the sampler. Cooling proceeds perpendicular to the sample analysis surface, so that the sample surface is very homogeneous.

The prechamber which precedes the sample chamber first reduces the inflow velocity of the melt, so that contaminants flowing in with the melt, such as slag particles or gases, move upward because of buoyancy. As a result of this purging process, the molten metal flowing into the sample chamber is largely free of such contaminants. Cooling of the molten metal in the sample chamber proceeds relatively slowly, so that on the one hand, contaminant particles in the sample chamber float upward and thus are removed from the sample to a greater degree. On the other hand, the slow solidification process makes it easier to detach the sample chamber from the prechamber in the region of the inlet duct, since it has been found that at the time when the sample chamber is detached, the molten metal in the region of the inlet duct has generally not yet completely solidified.

It is advantageous that the walls of the prechamber and the border of the inflow opening are made of a high-melting-point metal, for example steel. As a result the parts that are most highly stressed when the melt flows in are protected against damage, and the sample is protected from contamination by constituents of the sampler. Besides steel, it would also be possible to use refractory materials such as quartz or ceramic, or another high-melting-point metal. Preferably, the prechamber and the inlet duct are cylindrical in shape, the diameter of the prechamber being at least twice as great as the diameter of the inlet duct. It is useful if the diameter of the inlet duct is less than the diameter of the inflow opening. Such a configuration creates optimum conditions for quieting the melt and for uniform inflow into the sample chamber. In this connection, a diameter for the prechamber of approximately 22 to 50 mm, in particular 30 to 40 mm, and a diameter for the inlet duct of approximately 5 to 11 mm, in particular approximately 8 to 9 mm, have proved advantageous.

The wall thickness of the prechamber may suitably be approximately 2 to 10 mm, in particular 2.5 to 4 mm. This wall thickness guarantees both sufficient stability and adequate thermal insulation of the molten metal. It is advantageous that the inflow opening be arranged in the region of the prechamber facing toward the immersion end The result of delivering the molten metal to this end of the prechamber which faces toward the sample chamber is that the molten metal remains at least partly liquid in the region of the inlet duct until the sample is removed from the sampler, thus ensuring easier sample removal.

It is also possible to provide the sample chamber with two regions of different wall thickness; suitably, the wall thickness of the prechamber in the region of its immersion end is approximately 1 to 5 mm, and is approximately 2 to 10 mm in the region facing away from the immersion end, the inflow opening being arranged in the region with the greater wall thickness facing away from the immersion end. In particular, the wall thickness of the prechamber in the region of its immersion end can be approximately 1 to 2 mm, and approximately 3 to 4 mm in the region facing away from the immersion end. It is particularly advantageous, in the case of the two-part prechamber of this kind, that the region with the lesser wall thickness is approximately one to three times as long as the region with the greater wall thickness.

The surfaces that are directly exposed to the stream of molten metal flowing into the sample chamber are subject, because of the high energy of this molten metal, to very high thermal and mechanical stresses. The increased wall thickness in this region of the prechamber prevents the prechamber from being damaged by the inflowing molten metal, since both the thermal and the mechanical stability of the prechamber wall rises with increasing wall thickness. The region of the prechamber at the immersion end, whose wall is not exposed to the direct impact of the molten metal flowing into the prechamber, has a lesser wall thickness. This prevents too great a quantity of heat from being conducted from the molten metal to the wall, thus retarding solidification of the inflowing melt and promoting the precipitation of contaminants from the molten metal. The resulting retarded solidification also facilitates sample removal, as already explained above. In this case the retarder cap that is advantageously arranged in at the end of the quartz tube, which projects into the prechamber, also provides retardation. The buoyancy effect of the lighter contaminants in the molten metal is thereby improved.

Furthermore, it is advantageous that the flat sample chamber have at least two chamber regions with different thicknesses, arranged one behind the other as seen in the inflow direction, the chamber region with the greater thickness being arranged in the end of the flat sample chamber facing away from the immersion end. The buoyancy and escape of entrained contaminants brought into the sample chamber is also promoted by the fact that the greater thickness is arranged at the top in reference to the immersion direction.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there are shown the drawings embodiments which are presently preferred. It should be understood, however, that the invention is not limited to the precise arrangements and instrumentalities shown. In the drawings.

Detailed Description of Preferred Embodiments

The sampler has a carrier tube 1 which contains two paperboard tubes inserted one into the other, and in which the flat sample chamber 2 and prechamber 3 are arranged.

Figure 1:
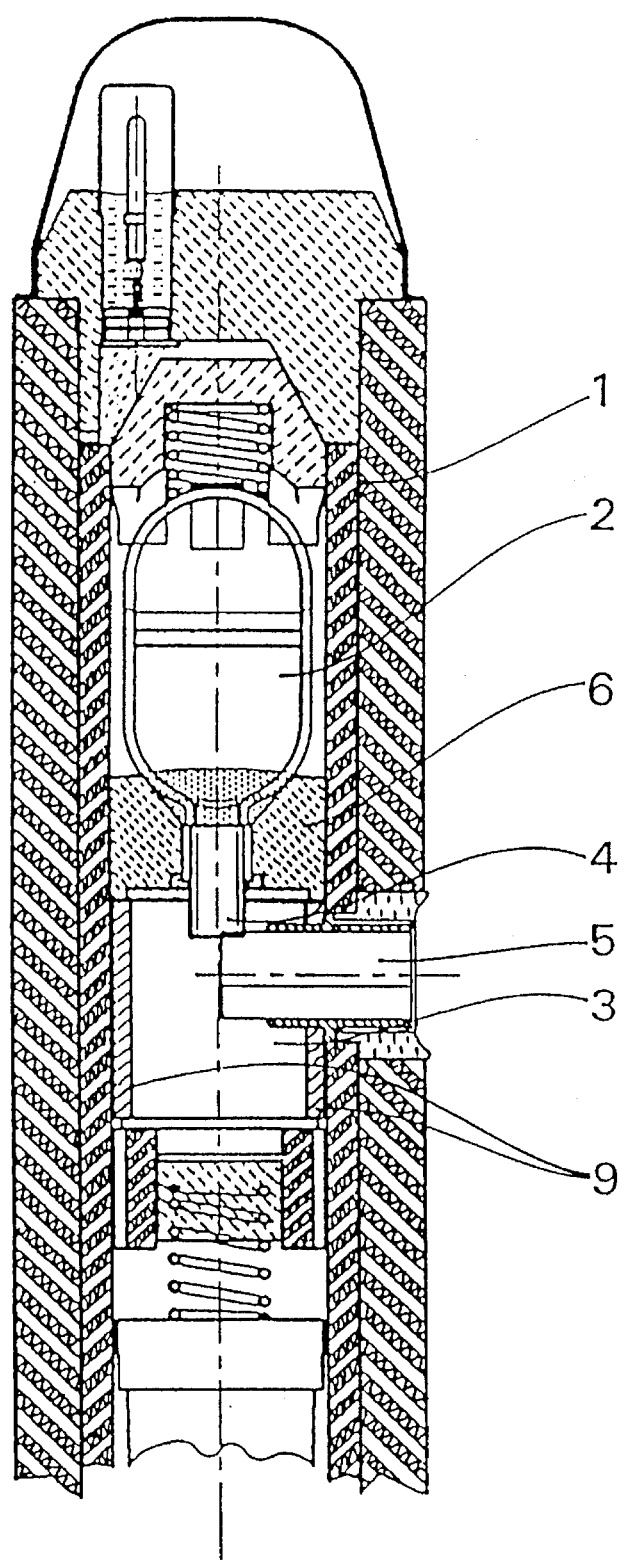
FIG. 1 shows a sampler according to the invention in lengthwise section.

The flat sample chamber 2 is arranged at the immersion end of the sampler. Arranged at the end of the flat sample chamber 2 facing away from the immersion end is an inlet duct 4, comprising a quartz tube, that connects the flat sample chamber 2 to the prechamber 3. The inflow opening 5 passes through the carrier tube 1 into the prechamber 3. An arrangement of this kind is shown in FIG. 1. The cross section of the prechamber 3 is greater in every direction than the cross section of the inflow opening 5 and of the inlet duct 4, in each case viewed transversely to the flow direction. As a result, before the molten metal flows into the flat sample chamber 1, it passes into a kind of buffer zone in which it is more or less quieted, whereby gravity will cause lighter contaminant particles and gas bubbles to move out of the region of the inlet duct 4.

To prevent premature solidification of the melt and to promote the buoyant movement of contaminants, both the prechamber 3 and the inlet duct 4 are cylindrical in shape, the diameter of the prechamber 3 being approximately 30 to 40 mm and the diameter of the inlet duct 4 being approximately 8 to 9 mm. The diameter of the steel-bordered inflow opening 5 is therefore greater than the diameter of the inlet duct 4. The thickness of the steel wall 9 of the prechamber 3 is approximately 2.5 to 4 mm. With these dimensions and the arrangement of the inflow opening 5 in the region of the prechamber 3 facing toward the immersion end, the molten metal that has flowed into the sampler remains liquid for a very long time, so that upon destruction of the inlet duct 4, the flat sample chamber 2 can be easily removed from the sampler. Also contributing to this result is the cement or ceramic insulation 6 that is arranged around the inlet duct 4 and is also in contact with both the flat sample chamber 2 and the prechamber 3. This insulation 6 also provides thermal isolation between the metal flat sample chamber 2 and the prechamber 3. This is particularly important in the embodiment depicted in FIG. 1, in which heat is continually being conducted into the region of the inflow duct 4 by the melt flowing into the prechamber 3.

Figure 2:
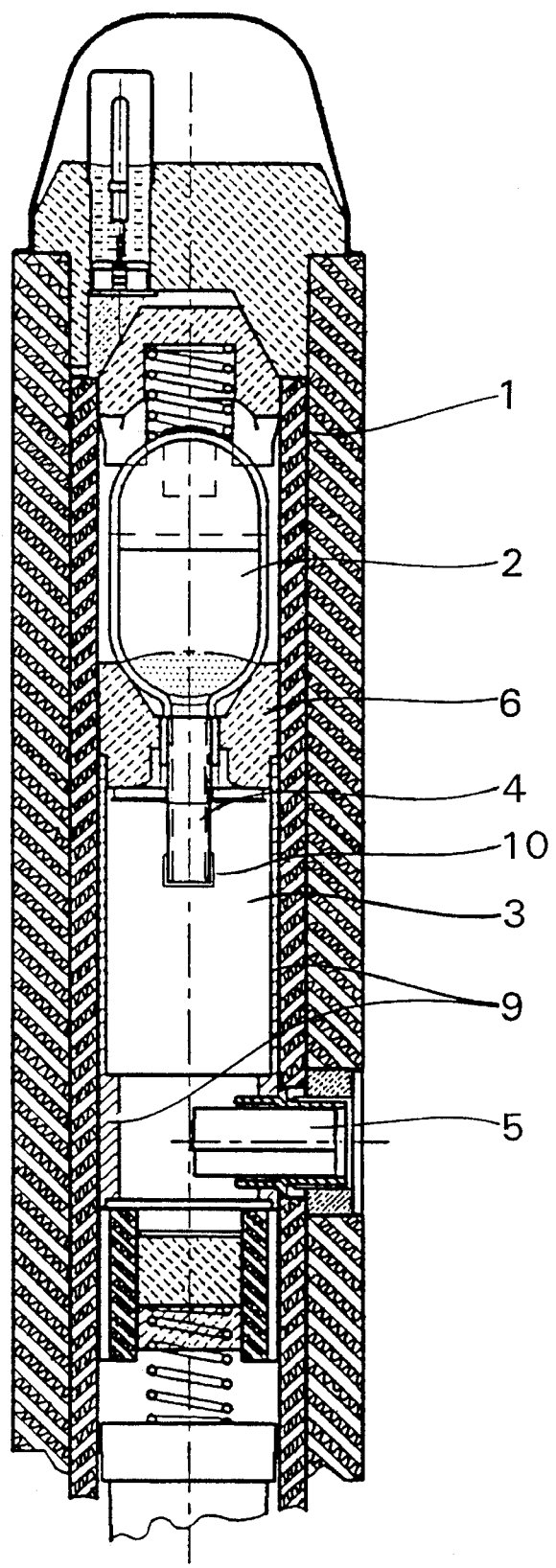
FIG. 2 shows a sampler according to the invention with a two-part prechamber in lengthwise section.

A further embodiment of the prechamber 3 is depicted in FIG. 2. Here the prechamber 3 has two regions of different wall thickness, one region with a wall thickness of about 1 to 2 mm being arranged in the region of the inlet chamber 3 facing toward the immersion end, i.e. toward the inlet duct 4, while the second region with a wall thickness of 3 to 4 mm, into which the inflow opening 5 opens, is arranged in the region of the prechamber 3 facing away from the flat sample chamber 2. Here the greater wall thickness in the region of the inflow opening 5 gives the prechamber 3 good resistance to damage from the molten metal shooting in at high speed, while the lesser wall thickness in the region of the inlet duct 4 prevents the extraction of too much heat from the molten metal through the wall 9, so that premature solidification of the molten molten in the prechamber 3 is prevented with this arrangement as well. A retarder cap 10 is arranged on the opening of the inlet duct 4 into the prechamber 3.

In both embodiments (according to both FIG. 1, and FIG. 2), the temperature of the molten metal is thus highest in the region of the prechamber 3, into which the inlet duct 4 opens. As a result, in this specific part of the prechamber 3 contaminants and gas bubbles can move very easily, on account of gravity, away from the flat sample chamber 2, and because of the lower melt viscosity resulting from its temperature, the melt flows very easily and without bubbles into the flat sample chamber 2. The flat sample chamber 2 has two chamber regions with different thicknesses, arranged one behind the other, the chamber region with the greater thickness being arranged in the end of the flat sample chamber 2 facing away from the immersion end. This is the region which the molten metal enters first, and which during sampling is arranged at the top as far as gravity is concerned, so that because of the arrangement of the prechamber 3, the gases contained in the flat sample chamber 2 also experience buoyant movement out of this region as well.

Figure 3:
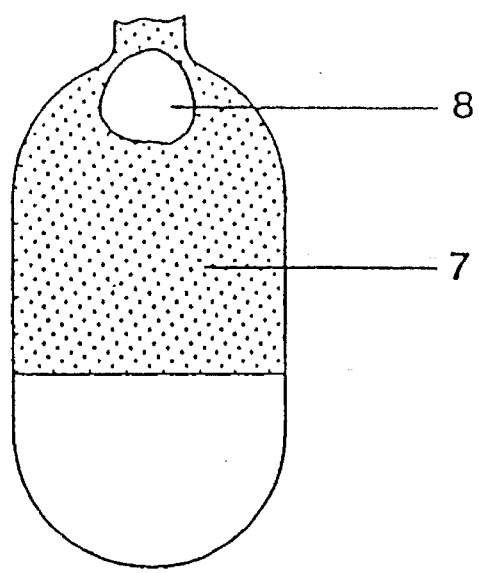
FIG. 3 shows a schematic representation of a sample obtained with the sampler according to the invention.
Figure 4:
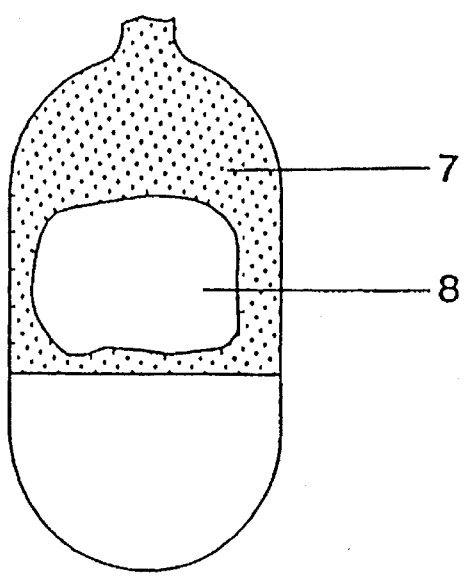
FIG. 4 shows a schematic representation of a sample obtained with a sampler according to the prior art.

The sampler just described can be used to obtain high-quality samples. FIG. 3 shows a schematic representation of such a sample 7. Depicted in the region with the greater thickness, shown in section, is a gas bubble 8 that has solidified in the region of the inlet duct 4, i.e. just before its removal from the flat sample chamber 2. FIG. 4, in contrast, represents a sample 7 obtained with a conventional sampler. A substantially larger bubble 8 has solidified in the center of the sample 7, since it was not possible for the gases to escape from the flat sample chamber 2. Such large gas bubbles 8, which are generally present in addition to a plurality of smaller gas inclusions, lead to erroneous analytical results, since these gas inclusions are irregularly distributed in the sample 7 and cannot be exactly localized. On the other hand, the gas bubbles 8 located only in the vicinity of the inlet duct 4 do not play a substantial role in the quantitative analysis of the sample 7.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An immersion sampler for molten metal comprising a hollow carrier tube (1) having a longitudinal axis and an immersion end, a flat sample chamber (2), arranged in the carrier tube, an inlet duct (4) with an inflow opening (5) arranged on an end of the flat sample chamber opposite to the immersion end of the carrier tube, said sample chamber having a wall surface which forms an analysis surface on a metal sample and, runs approximately parallel to the axis of the carrier tube, and a prechamber (3) arranged inside the carrier tube (1) at an end of the inlet duct (4) opposite to the immersion end of the carrier tube (1) above the flat sample chamber (2), and between the inlet duct (4) and the inflow opening (5), said prechamber (3) and said inlet duct (4) Being cylindrical in shape, said prechamber (3) having a cross-sectional area transverse to the direction of molten metal inflow through the inflow opening (5), which is greater than the cross-sectional area (diameter) of the inflow opening (5), and having a cross-sectional area transverse to the axis of the inlet duct (4) in the vicinity of its inlet which is greater than the cross-sectional area (diameter) of the inlet of the inlet duct (4), said prechamber (3) having a diameter at least twice as great as the diameter of the inlet duct (4) and the diameter of the inlet duct (4) being less than the diameter of the inflow opening (5), said prechamber (3) having at least two regions having different wall thickness, the wall thickness of said prechamber (3) in the region toward the immersion end being approximately 1 to 5 mm and being approximately 2 to 10 mm in the region facing away from the immersion end, the inflow opening (5) being arranged in the region with the greater wall thickness facing away from the immersion end.

2. A sampler according to claim 1, wherein walls (9) of the prechamber (3) and a border of the inflow opening (5) are made of a high melting point metal.

3. A sampler according claim 1, wherein the diameter of the prechamber (3) is approximately 22 to 50 mm.

4. A sampler according to claim 3, wherein the diameter of the prechamber (3) is approximately 30 to 40 mm.

5. A sampler according to claim 1, wherein the diameter of the inlet duct (4) is approximately 5 to 11 mm.

6. A sampler according to claim 5, wherein the diameter of the inlet duct (4) is approximately 8 to 9 mm.

7. A sampler according to claim 1, wherein the prechamber (3) has a wall thickness of approximately 3 to 10 mm.

8. A sampler according to claim 1, wherein the wall thickness of the prechamber (3) is approximately 2.5 to 4 mm.

9. A sampler according claim 1, wherein the inflow opening (5) is arranged in the region of the prechamber (3) facing toward the immersion end.

10. A sampler according to claim 1, wherein the wall thickness of the prechamber (3) in the region toward the immersion end is approximately 1 to 2 mm and is approximately 3 to 4 mm in the region facing away from the immersion end.

11. A sampler according to claim 1, wherein the region with the lesser wall thickness is approximately one to three times as long as the region with the greater wall thickness.

12. A sampler according to claim 1, wherein the flat sample chamber (2) has at least two chamber regions with different thicknesses, arranged one behind the other as seen in the metal inflow direction, the chamber-region with the greater thickness being arranged in the end of the flat sample chamber (2) facing away from the immersion end.

13. An immersion sampler for molten metal comprising a hollow carrier tube (1) having a longitudinal axis and an immersion end, a flat sample chamber (2), arranged in the carrier tube, an inlet duct (4) with an inflow opening (5) arranged on an end of the flat sample chamber opposite to the immersion end of the carrier tube, said sample chamber having a wall surface which forms an analysis surface on a metal sample and, runs approximately parallel to the axis of the carrier tube, and a prechamber (3) arranged inside the carrier tube (1) at an end of the inlet duct (4) opposite to the immersion end of the carrier tube (1) above the flat sample chamber (2), and between the inlet duct (4) and the inflow opening (5), said prechamber (3) having a cross-sectional area transverse to the direction of molten metal inflow through the inflow opening (5), which is greater than the cross-sectional area (diameter) of the inflow opening (5), and having a cross-sectional area transverse to the axis of the inlet duct (4) in the vicinity of its inlet which is greater than the cross-sectional area (diameter) of the inlet of the inlet duct (4), said prechamber (3) having at least two regions having different wall thicknesses, the wall thickness of said prechamber (3) in the region toward the immersion end being approximately 1 to 5 mm and being approximately 2 to 10 mm in the region facing away from the immersion end, the inflow opening (5) being arranged in the region with the greater wall thickness facing away the immersion end.

14. An immersion sampler for molten metal comprising a hollow carrier tube (1) having a longitudinal axis and an immersion end, a flat sample chamber (2), arranged in the carrier tube, an inlet duct (4) with an inflow opening (5) arranged on an end of the flat sample chamber opposite to the immersion end of the carrier tube, said sample chamber having a wall surface which forms an analysis surfacer on a metal sample and, runs approximately parallel to the axis of the carrier tube, and a prechamber (3) arranged inside the carrier tube (1) at an end of the inlet duct (4) opposite to the immersion end of the carrier tube (1) above the flat sample chamber (2), and between the inlet duct (4) and the inflow opening (5), said prechamber (3) having a cross-sectional area transverse to the direction of molten metal inflow through the inflow opening (5), which is greater than the cross-sectional area (diameter) of the inflow opening (5), and having a cross-sectional area transverse to the axis of the inlet duct (4) in the vicinity of its inlet which is greater than the cross-sectional area (diameter) of the inlet of the inlet duct (4), the flat sample chamber 2) having at least two chamber regions with different thickness, arranged one behind the other as seen in the metal inflow direction, the chamber region with the greater thickness being arranged in the end of the flat sample chamber (2) facing away from the immersion end.

* * * * *